(12) United States Patent
Saul et al.

(10) Patent No.: US 8,709,792 B2
(45) Date of Patent: Apr. 29, 2014

(54) LATERAL FLOW TEST KIT AND METHOD FOR DETECTING AN ANALYTE

(75) Inventors: Steven J. Saul, Arlington, MA (US); Mark E. Tess, Merrimack, NH (US); Robert J. Markovsky, Brentwood, NH (US)

(73) Assignee: Charm Sciences, Inc., Lawrence, MA (US)

( * ) Notice: Subject to any disclaimer, the term of this patent is extended or adjusted under 35 U.S.C. 154(b) by 421 days.

(21) Appl. No.: 12/842,484

(22) Filed: Jul. 23, 2010

(65) Prior Publication Data

US 2010/0285610 A1 Nov. 11, 2010
US 2013/0059399 A9 Mar. 7, 2013

Related U.S. Application Data

(62) Division of application No. 11/883,784, filed as application No. PCT/US2006/005484 on Feb. 16, 2006, now Pat. No. 7,785,899.

(60) Provisional application No. 60/654,292, filed on Feb. 18, 2005.

(51) Int. Cl.
*C12M 1/34* (2006.01)
*G01N 33/558* (2006.01)

(52) U.S. Cl.
CPC ............. *G01N 33/558* (2013.01); *Y10S 435/97* (2013.01); *Y10S 436/81* (2013.01)
USPC ............ 435/287.7; 422/50; 422/70; 422/412; 422/420; 422/425; 422/82.05; 435/287.1; 435/287.8; 435/970; 435/4; 435/7.1; 435/287.2; 435/287.9; 435/288.7; 436/514; 436/518; 436/810; 436/538; 436/536; 436/539; 436/540; 436/541; 436/161; 436/162

(58) Field of Classification Search
USPC ................. 422/50, 70, 412, 420, 425, 82.05; 435/287.1, 287.7, 287.8, 970, 4, 7.1, 435/287.2, 287.9, 288.7; 436/514, 518, 436/810, 538, 536, 539, 540, 541, 161, 162
See application file for complete search history.

(56) References Cited

U.S. PATENT DOCUMENTS

| | | | |
|---|---|---|---|
| 4,703,017 A | 10/1987 | Campbell et al. | |
| 5,229,073 A | 7/1993 | Luo et al. | |
| 5,384,264 A | 1/1995 | Chen et al. | |
| 5,451,504 A * | 9/1995 | Fitzpatrick et al. | 435/7.2 |
| 5,569,608 A | 10/1996 | Sommer | |
| 5,602,040 A | 2/1997 | May et al. | |
| 5,798,273 A | 8/1998 | Shuler et al. | |
| 5,874,216 A * | 2/1999 | Mapes | 435/6.11 |
| 5,985,675 A | 11/1999 | Charm et al. | |
| 6,136,610 A | 10/2000 | Polito et al. | |
| 6,183,972 B1 | 2/2001 | Kuo et al. | |

(Continued)

OTHER PUBLICATIONS

International Search Report and Written Opinion for PCT/US06/05484 from Patent Cooperation Treaty; pp. 1-6.

*Primary Examiner* — Melanie Y Brown
*Assistant Examiner* — Erik B Crawford

(57) ABSTRACT

A method and device for detecting analytes in a test sample. Embodiments include methods for quantitatively detecting analytes within a range of concentrations. In an embodiment the method includes a lateral flow test strip with multiple test areas for capturing a labeled receptor to provide a detectable signal.

22 Claims, 6 Drawing Sheets

(56) References Cited

U.S. PATENT DOCUMENTS

| | | |
|---|---|---|
| 6,319,466 B1 | 11/2001 | Markovsky et al. |
| 6,436,721 B1 | 8/2002 | Kuo et al. |
| 6,475,805 B1 | 11/2002 | Charm et al. |
| RE38,430 E | 2/2004 | Rosenstein |
| 6,924,153 B1 | 8/2005 | Boehringer et al. |
| 7,144,742 B2 | 12/2006 | Boehringer et al. |
| 2007/0243630 A1 | 10/2007 | Boehringer et al. |

* cited by examiner

LATERAL FLOW TEST KIT AND METHOD FOR DETECTING AN ANALYTE

REFERENCE TO PRIOR APPLICATIONS

This application is a divisional application of U.S. patent application Ser. No. 11/883,784, filed Aug. 6, 2007, now U.S. Pat. No. 7,785,899, issued Aug. 31, 2010, which is the national stage of International Application. No. PCT/US06/05484, filed Feb. 16, 2006, which claims the benefit of the filing date of U.S. Provisional Patent Application. Ser. No. 60/654292, filed Feb. 18, 2005, hereby incorporated by reference.

FIELD OF APPLICATION

The application relates to detecting an analyte, such as a small molecule, in a sample using a solid support such as a lateral flow type test strip.

BACKGROUND

Tests to detect analytes in samples are known in the art. Some examples are described in U.S. Pat. No. 5,985,675, issued Nov. 16, 1999; U.S. Pat. No. 6,319,466, issued Nov. 20, 2001; U.S. patent application Ser. No. 10/289,089, filed Nov. 6, 2002 (based on U.S. Provisional Application 60/332,877, filed Nov. 6, 2001); U.S. patent application Ser. No. 09/961,998, filed Sep. 24, 2001, and U.S. patent application Ser. No. 10/993,340, filed Nov. 19, 2004, all of which are incorporated herein by reference in their entirety.

SUMMARY

Figure 1:
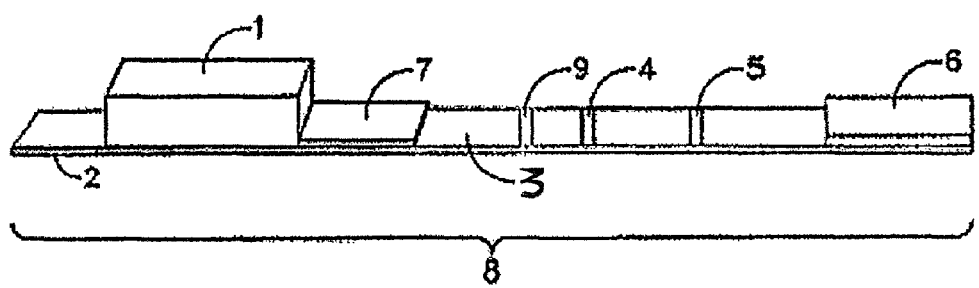
FIG. 1 is a side view of an embodiment having two test areas 9, 4 and a control area/zone 5.

One aspect involves a method for the analysis of a liquid sample for the presence of an analyte in which the sample is contacted with a receptor to form a mobile phase. The receptor can be characterized by an ability to bind to analyte to provide, in the mobile phase, a receptor-analyte complex.

The mobile phase contacts, or is put into contact with, a first test area on a solid support. The solid support can be configured to allow the mobile phase to flow from the first test area to a second test area on the solid support and, if a control zone is included, to the control zone. The first test area can include a capture agent immobilized on the solid support. The first test area capture agent will have greater binding affinity to the receptor than to the receptor-analyte complex. As a result of that differential in binding affinity, captured receptor in the test area will decrease as sample analyte concentration increases. The second test area can also include a capture agent immobilized on the solid support. As with the first area capture agent, the second test area capture agent will have greater binding affinity to the receptor than to the receptor-analyte complex. The capture agent can be the same in each of the test areas and at the same or different concentrations in each area. The capture agents can also be different, for example with different binding characteristics to the receptor.

The receptor can be labeled with a label, such as a colored particle, that can be detected when the receptor is bound to the solid support via capture by the capture agent immobilized on the solid support. The intensity of the detectable signal, for example a visible signal, at the first and second test areas can be measured to determine a result. In an inhibition style test the strength (intensity) of the signals are inversely related to the concentration of analyte in the sample. The signal intensities can be observed visually or measured by an electronic test instrument. For example the intensity at each of the two test areas can be summed to determine a result that can relate to the concentration of an analyte in the sample.

In another embodiment a control zone is included. The control zone can include a control zone capture agent on the solid support. The control zone capture agent can have affinity to the receptor that is equivalent to the control zone capture agent's affinity to the receptor-analyte complex. When the control zone capture agent has affinity to the receptor that is equivalent to its affinity to the receptor-analyte complex, the signal in the control zone will increase as analyte concentration in the sample increases. The control zone can be compared to the test areas to determine the result. In an example a digital reading, related to signal intensity, is provided by an electronic instrument that calculates the intensity differences between the first and second test areas and the control zone and sums the results to arrive at the approximate concentration of analyte in the sample, for example by comparing the test result to a predetermined value. A variety of reading methods can be employed depending on the label used. When the label is a colored particle, such as a gold particle, the reader can be a reflectance reader.

The solid support can be a lateral flow test strip with a stationary phase membrane on which the test and control zones are placed. The membrane can allow lateral capillary flow of the sample from the first end to the second end and has the test areas thereon.

In some embodiments the receptor is labeled prior to application to the test strip. In other embodiments the label can be contacted with the receptor during test operation. The receptor can be an antibody such as an antibody to an analyte such as a mycotoxin, for example, aflatoxin or other small molecules such as antibiotics.

Control zone capture agents can include antibody binding proteins such as protein A and/or antibodies such as anti-species antibody. The capture agent can be immobilized directly on the solid support or through attachment to a carrier protein. The control zone can be used for comparison to the test areas and also can be used to inform the user that the mobile phase has flowed through the test strip and/or that the test is functioning properly. In that sense the control zone can be used as a flow control. The control zone can also be involved in a reaction that is independent of the analyte-receptor reaction. In that way the control zone can provide, if desired, a consistent signal that does not vary with concentration of analyte. Such an independent reaction can include providing a separate labeled receptor with affinity only to the control zone capture agent.

DESCRIPTION

Lateral flow type test strips are an example of a test utilizing a solid support to capture a detectable signal. Lateral flow tests can be used to detect one or more substances (analytes) in a fluid sample. Lateral flow strips generally include a stationary phase and a mobile phase. The stationary phase can include various reagents immobilized on the test strip. The mobile phase can include the fluid sample that flows over and/or through the test strip. The mobile phase can also include a variety of reagents. As the mobile phase flows it also can carry with it reagents that may be reconstituted from the strip. The mobile phase can also include solutions, such as dilution buffer. As an alternative to reconstitution from the strip, mobile phase reagents can be mixed with the sample prior to application of the sample to the strip.

Reaction of a substance in the mobile phase with a stationary phase reagent can generate a detectable signal. The stationary phase reagents, sometimes referred to as capture agents, can be immobilized on the strip so that they capture substances from the mobile phase. The signal can be generated by a reagent from the mobile phase, often referred to as a label, which attaches to one or more of the stationary phase reagents. Various suitable labels include chromogens, catalysts, fluorescent compounds, chemiluminescent compounds, radioactive labels, magnetic beads or magnetic particles, enzymes or substrates, vesicles containing signal producing substances, colorimetric labels, direct visual labels including colloidal metallic and metallic and non-metallic colored particles, dye particles, or organic polymer latex colored particles.

To detect the presence or absence of an analyte test strips can be designed to provide a signal that can be observed visually, such as color changes or color differences on the test strip. The signal can also be observed, measured and/or interpreted visually or with a reader. A variety of readers are appropriate including spectrophotometers, LCD cameras, reflectance readers, luminometers, fluorometers, scintillation counter, magnetic detectors and other instruments capable of reading, measuring and/or interpreting changes on a lateral flow test strip. One such instrument is described in U.S. Pat. No. 6,124,585, issued Sep. 26, 2000, hereby incorporated by reference. Another such instrument is a ROSA® Reader (ROSA® is a registered trademark of Charm Sciences, Inc., Lawrence, Mass.).

Presence or absence tests, known in the art as qualitative tests, provide a yes or no result. Tests that detect the presence or absence of a target analyte above or below a certain threshold level are known as semi-quantitative tests. Tests that determine that a target analyte is present at a particular concentration, or within a range of concentrations, are known as quantitative tests. Although quantitative tests may determine that an analyte is present within a range of concentrations or at a particular level the results also have a range of error. For example, a result that an analyte is present at 25 parts per billion (ppb) can be within a range of acceptable error, for example a result of 25 ppb can mean that analyte is present in a range of 20-30 ppb. Such a test is referred to as quantitative. Tests that provide quantitative results within a limited range are also described as quantitative. For example, results may indicate that an analyte is present within a range of 0 to 100 ppb but above 100 ppb no conclusion can be drawn other than that the result is above 100 ppb.

Quantitative results are sometimes preferred or required. For example, the United States Department of Agriculture, Grain Inspection, Packers and Stockyard Administration, Federal Grain Inspection Service, Program Notice FGIS-PN-04-15, dated Jun. 16, 2004, describes performance criteria for test kits. Criteria for aflatoxin in corn include quantitative detection at 5 ppb, 10 ppb, 20 ppb and 100 ppb total aflatoxin (B1+B2+G1+G2). One of the herein described embodiments includes a lateral flow test strip that meets those criteria. Various embodiments can be used with a variety of matrices including those where the most pronounced contamination has been encountered, including a variety of nuts, including, for example, tree nuts and peanuts, and feeds and grains including corn, corn byproducts, soybeans, rice, sorghum, wheat and barley, oilseeds and cottonseed.

Although, many of the herein examples and descriptions refer to detecting aflatoxin, other analytes can be detected and quantified in a variety of matrices using the herein described methods and devices. For example, some embodiments can be used to detect aflatoxin, including aflatoxin M1 and M2, in milk. Other possible target analytes include hormones, vitamins, drugs, metabolites and their receptors and binding materials, antibodies, peptides, protein, allergens, fungicides, herbicides, pesticides and plant, animal and microbial toxins may be determined using the present methods and apparatuses. Other analytes that may be determinable by the disclosed methods and apparatuses include antibiotics, such as beta-lactams, cephalosporins, erythromycin, sulfonamides, tetracyclines, nitrofurans, quinolones, vancomycin, gentamicin, amikacin, chloramphenicol, streptomycin and tobramycin, toxins, such as mycotoxins, vomitoxin and drugs of abuse, such as opioids and the like, as well as the metabolites thereof.

A lateral flow strip upon which various reagents and/or sample are applied can be wholly or partially porous or bibulous so that a mobile phase can flow on or through the strip. The strip can also be wholly or partially of a material, for example nitrocellulose, that can bind proteins. A variety of materials can be used in various portions of the strip including natural or synthetic materials including cellulosic materials such as paper, cellulose and cellulose derivatives such as cellulose acetate and nitrocellulose; fiberglass; glass fiber filter, for example WHATMAN® Fusion 5 membrane (Whatman® is a registered trademark of Whatman Paper Limited, Kent, England); cloth, both naturally occurring and synthetic; porous gels such as silica gel, agarose, dextran and gelatin; porous fibrous matrices; starch based materials, such as cross-linked dextran chains; ceramic materials; films of polyvinyl chloride and combinations of polyvinyl chloride-silica; POREX® (Porex® is a registered trademark of Porex Technologies Corp., Fairburn, Ga.) and the like. Generally, the material used in the flow stream should allow liquid to flow on or through the strip. If a variety of materials are used they can be in fluid flow communication/contact or capable of being brought into fluid flow communication/contact. The strip should have sufficient inherent strength or additional strength can be provided by a supplemental support such as a plastic backing upon which porous or bibulous strip components are attached.

In an embodiment an application pad is used. The application pad is in fluid flow communication/contact with a first end of a test strip. Contact can be either through direct contact or through an intermediate material allowing flow between the application pad and other portions of the test strip. The fluid flow communication/contact is such that the test sample can migrate from the application pad to the other portions of the test strip. In addition to receiving the sample, the application pad can also be used to drive fluid flow along the strip. Particles that are above a certain size may clog the strip pores or may interfere with flow due to affinity to strip components thereby causing invalid or incorrect test results or otherwise reduce test function. The application pad, and other strip components, can also serve as a filter to remove, from the sample, such particles.

In another embodiment, rather than pipette a pre-measured volume onto the strip, the test strip is arranged to be dipped into a sample to absorb a selected amount of the sample.

Mobile phase reagents can be applied to the application pad or to other portions of the test strip, for example a POREX® strip or a nitrocellulose membrane, prior to sample application. Alternatively, mobile phase reagents can be pre-mixed with the sample prior to applying the sample to the strip.

When mobile phase reagents are pre-applied to the strip, application of the sample reconstitutes the reagents for flow to portions of the test strip such as an area where stationary phase reagents are immobilized onto the test strip. Stationary-phase areas of the strip can include test zones and control zones.

Mobile phase reagents can include one or multiple receptors. Receptors can be selected for their affinity to a target analyte. The receptor may be any agent, for example, a receptor, enzyme, membrane protein, hormone, antibody or antibody fragment, that binds with appropriate specificity to the analyte in the test sample to form an analyte-receptor complex. The receptor can be detected through an attached label. Colloidal gold particles are an example of a useful label.

The receptor can be arranged to flow in the mobile phase and be captured by a stationary phase reagent. Locations on the test strip where receptors can be captured include a test zone and control zone. Either the test zone or control zone can include one or multiple capture areas. The test and/or control areas can be in a variety of configurations including, as commonly described, lines, dots or other configurations.

Stationary phase capture agents can be previously immobilized onto the test strip in either or both the test zone and control zone. Capture agent immobilization to the test strip can be through protein interaction with the solid support or various other immobilization techniques known in the art. For example, nitrocellulose is employed for its protein binding capacity. Capture agent immobilization can also be through size limitation immobilization.

The label, for example a label bound to the receptor, can be detected when captured by the immobilized capture agent. To detect multiple analytes, a test strip can have multiple test areas with different capture agents on each, or combined test areas with different capture agents in the same test area, to detect analytes collectively. Multiple test areas can also be employed with the same or similar capture agents in the same or different concentrations to detect a single analyte. When the same or similar capture agents are used the multiple test areas can be employed to increase the binding potential of the test zone. An increased binding potential means that more labeled receptor can bind within the test zone.

In an embodiment of a competitive inhibition binding test, a receptor for the analyte is labeled with a visible marker. The receptor flows with the sample in the mobile phase to a test zone. The capture agent immobilized at the test zone has affinity to the receptor that is the same or similar to that of the analyte in the test sample. Such a capture agent can be, for example, a representative analyte or analogue thereof that binds to generally the same portion, or binding site, on the receptor as does the analyte. Due to that affinity, capture agent at the test zone can bind receptor from the mobile phase more efficiently if the receptor is not bound by analyte from the sample. When the sample contains analyte, an analyte-receptor complex will form that wholly or partially prevents capture of the receptor at the test zone. As the amount of analyte in the sample increases, less receptor is captured at the test zone until the binding at the test zone compares only to the background signal.

When the binding potential at the test zone is high, the range of detectable analyte concentrations can be wide. When the binding potential at the test zone is low, the overall detection range tends to be narrower and the maximum distinguishable concentrations tend to be lower. Minimizing the test zone binding potential can, however, help increase test sensitivity.

One method for minimizing test zone binding potential includes minimizing the amount of receptor and/or label. Another method includes minimizing the amount of test zone capture agent. These methods can also be employed together to titrate the amount of binding pair (receptor/capture agent) materials to generate an assay to detect the analyte within a defined test range.

When test zone binding potential is minimized, a smaller amount of analyte may result in a relatively larger ratio of analyte-receptor complex compared to non-complexed receptor and, therefore, relatively less capture at the test zone. Although test sensitivity may be maximized the detection range may be narrower as well.

A method for maximizing the available range of test zone binding is to maximize binding potential at the test zone, for example by maximizing the amount of receptor/label and/or maximizing the amount of capture agent. A possible problem with this approach is that results in the low range of sensitivity may be indistinguishable. For example, a negative sample will have maximum binding at the test zone and a low level of analyte may inhibit some binding at the test zone. However, so much excess binding potential may remain that the difference in binding compared to a negative sample may not be readily discernible.

One embodiment is a method for maximizing binding potential, while maintaining test sensitivity. Such an embodiment includes using multiple test areas, within the test zone, each test area being capable of capturing the receptor. The multiple test areas can each contain the same or similar concentrations of capture agent. Alternatively, the test areas can contain different concentrations of capture agent. For example, the first test area can have a lower concentration of capture agent as compared to the second test area. Such a configuration can accommodate that receptor arrives at the first test area earlier and, therefore, everything else being equal, more binding will tend to occur in the first test area compared to the second. That is, with an equal amount of capture agent at each area, there would be more receptor available for binding to the first test area which would result in more binding to the first test area as compared to the second test area. If that is not desirable then capture agent can be titrated accordingly.

Another method for maximizing binding potential in the test zone, while maintaining test zone sensitivity, includes using a wider test zone. Spreading the capture agent over a larger area, similar to using multiple test areas, can allow greater result discrimination and low level detection.

When receptors are antibodies or fragments thereof, capture agents can include antigens with affinity to the antibody, including analyte, analogues thereof, or any substance exhibiting affinity to the receptor that is similar to that of the analyte. When using multiple test areas to capture the same receptor, each area can have the same capture agent. Each area can also have a different capture agent if the different capture agent has affinity to the same binding sites or areas as does the receptor.

A control zone can be used for comparison to the one or more test areas or as a signal that the test functioned properly and is complete. The control zone can include a substance as a capture agent that has equivalent affinity to the mobile phase receptor whether or not the receptor is bound by analyte from the sample. For example, the control zone can include a substance that binds to a different portion of receptor than does the analyte. As a result, binding of analyte to receptor to form a complex will not significantly change the binding affinity of the control zone capture agent to the receptor. Particularly when such a control zone is on a test strip in which mobile phase contacts the control zone after contacting the test zone, the test can be titrated to bind less receptor in a negative sample and more receptor as the concentration of analyte in the sample increases.

When the amount of receptor in the test system has been increased the binding potential of label to the test zone binding also increases. A second test area can be added that binds some of the increased potential and thereby reduces the amount of receptor available to bind in the control zone. With increasing analyte in the sample the control zone will get correspondingly darker as less label binds to the test zone and subsequently more label becomes available for binding in the control zone. Employing multiple test areas within the test zone to capture receptor can be usefully employed to allow the control zone to be used to increase the range of detection for the test system.

In another embodiment the control zone capture agent can include a capture agent that will capture a substance, conjugated to the receptor or label, which does not react with the analyte. In an example for detection of aflatoxin, in which aflatoxin antibody is conjugated to a detectable label, a second antibody, or other substance, can be conjugated to a different label. In this way the control zone can be designed to bind that second antibody that does not react with aflatoxin and, therefore, provide a consistent signal that changes little whether the sample is positive or negative.

Some useful control zone capture agents include antibody binding proteins such as protein A, protein G or protein AG and recombinant forms of the same. Control zone capture agents can also include an antibody, such as an anti-species antibody, alone or in combination with other antibody binding proteins. When control zone capture agents are proteins, and a solid support that binds protein, such as nitrocellulose, is used, the capture agent can be applied directly to the support. For improved binding to the support, the control line can also include a protein-protein conjugate with one being the capture agent and the other being a carrier protein. Useful carrier proteins include, for example, bovine serum albumin (BSA), keyhole limpet hemocyanin, thyroglobulin, ovalbumin, and various synthetic polypeptides such as poly-L-lysine, poly-L-glutamic acid, and polyethylenimine.

In a quantitative test, the changes in the test areas, and, when a control zone is present, the extent of the difference between the control zone and test zone or test areas, can determine the test range detection level of analyte. To accurately and/or numerically assess the differences and the binding at the control zone and test zone, particularly in a quantitative assay, a reader, such as a spectrophotometer or other reflectance/absorbance reader can be used to detect and/or measure the signal provided by a chromogen such as colloidal gold.

There are a number of possible methods for reading a result on a strip. In a strip with only one test area and one control area the control area can be compared to the test area. In a strip containing multiple test areas possible reading methods include: finding the difference in signal intensities between the control area and each of the test areas and adding the results; finding the difference in signal intensities between one test area and the control area; finding the difference in signal intensities between only one test area and control area for one set of conditions and the other test area and the control area for another set of conditions.

Using the sum of the difference in reflectance between the control area and the two test areas can provide a greater separation between results from a range of concentrations as compared to using only the difference between the control area and a single test area. Using the sum of the differences between the control areas and each of the two test areas, can also help to reduce testing error. For example, if an aberrant result occurred at one or the other test areas that result can be moderated by being combined with a second set of results. This can be particularly useful when quantitation at a particular concentration, or within a range of concentrations, occurs.

For quantitation, reflectance results can be converted to a concentration value for an amount of analyte. One method for converting reflectance to concentration can employ fitting the data to a curve using a formula, such as:

$$\text{concentration} = e^{\left(\frac{\text{Result}-c}{a}\right)} - b,$$

where a, b and c are constants determined by fitting the data to a curve.

The result is the value determined by comparing reflectance in the control area to reflectance at each of the test areas. For example, intensity values at each of the test areas can be separately deducted from intensity value at the control area and the two differences added together to arrive at the result. A look-up table can also be used to convert the mathematical result to a concentration value for the analyte.

In another embodiment, the test can be used not only as a quantitative test in which a reader provides a result in, for example, parts per billion (ppb) levels but also a qualitative result. For example, the control area can be compared visually with the first test area to determine that an analyte is present above a certain threshold level, for example above 10 ppb or above 20 ppb.

Many sample matrices, such as solid or granular materials, require an extraction of analyte into a liquid matrix before application to a solid support such as a test strip. For example, corn can be ground to pass through a 20-mesh sieve. The ground sample, for example 10 grams (g) or 50 g, can be extracted with 70% methanol in a 2:1 ratio (2 mL per 1 g of sample). Other extraction solvents can also be used including, for example, acetonitrile, ethanol or other concentrations of methanol, for example at 50%, 60%, 80% etc. Other extraction ratios can also be used, for example 5:1 extraction.

An extraction can take place using a variety of methods including: shaking the sample in a container, mixing the sample with a stirrer, or mixing the sample with a blender.

An extract can be obtained also by using a variety of methods including filtering to collect the extract, allowing sample to sit to form an extract layer above the ground sample, or centrifuging a portion of the sample to obtain an extract layer and sample layer.

For lateral flow assays, the sample or, if extraction is required, the sample extract, can be mixed with a dilution buffer that allows a mobile phase to flow uniformly over the test strip and/or allows reconstitution of the dried reagents on the test strip. The extract can be diluted by a number of methods and a variety of possible dilution ratios of the extract with the dilution buffer. The dilution buffer can consist of, for example, BSA solution, buffer or water. When the analyte is in sample liquid, such as fluid milk, the sample may not require dilution or extraction. Dilutions or extractions, however, may still be desirable such as to alter the test sensitivity range or to allow consistency between samples.

The membrane containing the beads can be pretreated with blocking solution that dissolves when the diluted sample is added. The nitrocellulose membrane can also be pretreated and/or blocked.

The test area and control area placement on the strip can be varied to adjust assay time. For example, a test strip utilizing 12 minute incubation may have the test and control areas immobilized further from the sample application pad as compared to a test strip using only 10, 8 minute or less incubation time. To shorten the incubation time, it may be possible to move the various areas closer to the sample application point. Examples of possible locations, measured from the application end of the test strip, include respective lines for the bottom ($1^{st}$ test area), middle ($2^{nd}$ test area) and top (control area) at 13 millimiter(mm)/17 mm/21 mm line spacing or 17 mm/21 mm/25 mm line spacing. Although the spacing shown is equal, equal spacing may not be necessary. The sensitivity of the assay may change depending on line positioning and, therefore, reagent titration can be adjusted to accommodate these differences or assay requirements.

EXAMPLE 1

Lateral Flow Quantitative Method for the Detection of Zero to 100 ppb Aflatoxin

Test Strip Overview

In this example the test strip included nitrocellulose, a POREX® membrane, a sponge and a disposal pad all in fluid flow contact/communication. The materials were arranged as shown FIG. 1 and secured to a plastic backing for support. The strip assembly was encased within a plastic housing in which the sponge portion of the housing was smaller than the fully expanded sponge.

The sponge was the sample application pad. The test strips were placed in a stainless steel incubator block carved to fit the test strips and heated to 4° C. When sample, including dilution buffer, was applied to the sponge it expanded within the confines of the housing allowing liquid sample to flow to and along the POREX® portion of the strip. As the sample flowed along the POREX® strip it contacted colloidal gold particles with aflatoxin antibody (the receptor) bound to the surface (gold-AB), creating the mobile phase. The mobile-phase, with gold-AB and sample, flowed onto the nitrocellulose membrane material from the POREX®. On the nitrocellulose membrane were two test areas and one control area. The two test areas each had concentrations of immobilized capture agent that would bind the sites of the gold-AB in the absence of previous binding to analyte in the sample. With aflatoxin present in a sample, sites of the gold-AB bound to aflatoxin in the sample. This binding decreased the gold-AB binding to the test areas and, therefore, decreased the intensity as measured by the reader at each of the test areas Inhibition of gold-AB to capture at the test areas resulted in more gold-AB available for binding to the control area and, therefore, the intensity of the control area increased. Control area capture agent included antibody binding protein.

Test Strip Detail

The AB (receptor) portion of the gold-AB was a rabbit immunoglobulin created from injecting a rabbit with a Bacillus Thuringensis (BTI)—aflatoxin immunogen. The antibody was purified starting from 5 ml of rabbit serum. To the 5 ml of serum was added 5 ml of PIERCE® binding buffer (PIERCE® is a registered trademark of Pierce Biotechnology, Inc., Rockford, Ill.) and the mixture was added to a protein A column. After washing the column, the antibody was eluted from the gel with PIERCE® elution buffer. The active fractions were pooled and subjected to a 50% ammonium sulfate (29.1 grams per 100 ml at 0° C.) fractionation. The precipitate was collected by centrifugation and the pellet was dissolved in 2 mM diethanolamine buffer, pH 8.0, and then the solution was desalted on a BIO-RADO® 10DG desalting column (BIO-RAD® is a registered trademark of BIO-RAD Laboratories, Hercules, calif.) equilibrated with 2 mM diethanolamine buffer, pH 8.0. To the desalted antibody was added 1.6 ml of BIO-LYTE® 6/8 AMPHOLYTE (BIO-LYTE® is a registered trademark of BIO-RAD Laboratories, Hercules, calif.) and this sample was added to a ROTOFOR® (ROTOFOR® is a registered trademark of BIO-RAD Laboratories, Hercules, calif.) cell for preparative isoelectric focusing. After the first ROTOFOR® run, fractions from about pH 7.0 to pH 7.8 were collected and subjected to a second run on the ROTOFOR® system. Fractions from about pH 7.0 to pH 7.7 were pooled for binding to gold beads (the label).

To form the gold beads, 1 ml of a filtered 40 mg/ml gold chloride solution is added to 360 ml of boiling water in a clean one liter flask. To 35 ml of water was added 3.5 ml of 1% sodium citrate solution. The citrate solution was added to the gold solution while boiling. After refluxing for 20 to 30 minutes the bead solution was cooled and brought to pH 8 with potassium carbonate.

Gold-AB were prepared by combining colloidal gold particles with the rabbit anti-aflatoxin antibody at 4000 U of activity per 400 ml of colloidal gold beads at pH 8.0 while stirring. One unit of antibody activity is determined by binding 1000 cpm of tritiated aflatoxin B1 in a 5 minute binding assay at 35° C. using IgGsorb® (IgGsorb® is a registered trademark of Stanley E. Charm, dba, The Enzyme Center, Lawrence, Mass.). IgGsorb® includes formalin-fixed *Staphylococcus aureus* cells containing protein A as a capture agent for the tritiated aflatoxin-antibody complex.

The gold-AB beads were mixed at room temperature for 20 minutes and then blocked with a blocking buffer (20 mM potassium phosphate, pH 7.2, containing 5% BSA, 0.05% BIOTERGE® (BIOTERGE® is a registered trademark of Stephan Company, Northfield, Ill.), 0.025% Tween 20 and 0.0155% PROCLIN® 5000 (PROCLIN® is a registered trademark of Rohm and Haas Company, Philadelphia, Pa.)) for at least one hour. The beads were centrifuged at 9500 rpm for 50 minutes in a SLA-3000 rotor. The bead pellet was dissolved in water and then bead storage buffer and then diluted to an absorbance of 0.167 per 10 microliters in 3 ml of a storage buffer. Glycerol was added to the bead solution to a final concentration of 16.7%. This bead solution was further diluted to 30% with bead spray solution (0.01 M sodium phosphate, pH 7.4, containing 10% BSA and 40% sucrose). For example 25% beads would contain 1 part beads to 3 parts bead spray solution. Storage buffer includes: 0.02M potassium phosphate, pH 7.2, containing 0.2% BSA, 0.05% BIOT-ERGE®, 0.025% TWEEN 20 and 0.155% PROCLIN® 5000.

The gold-AB was sprayed (4 lines at 0.8 µl/cm) using a BioDot sprayer onto POREX® (POREX® is a registered trademark of Porex Technologies Corp., Fairburn, Ga.). The POREX® was pretreated with 2 mM borate at pH 7.4, containing 0.1 M NaCl, 1% sucrose, 0.0025% SDS and 0.05 mg/ml reduced glutathione and dried.

The test zone with test areas and the control zone with a control area were sprayed onto a SARTORIUS® UNISART® CN-140 nitrocellulose membrane (SARTORIUS® and UNISART® are registered trademarks of Sartorius AG, Gottingen, Germany). The test and control areas were sprayed onto the nitrocellulose with a BioDot sprayer. In this example, the test areas were located at 17 mm and 21 mm as measured from the first end of the nitrocellulose membrane. Each area had a width of 0.6 to 1.0 mm. The test area spray solution contained BSA conjugated to an aflatoxin B1 derivative (BSA-B1). In this example, the 21 mm line contained a higher concentration of the conjugate (0.0525 mg/ml of BSA-aflatoxin for the first test area and 0.084 mg/ml for the second test area).

To prepare the test area spray solution aflatoxin BSA-B1 was added to 10 mM sodium phosphate buffer, pH 6.95, containing 20% sucrose and PROCLIN® 5000. To make the BSA-B1 conjugate, aflatoxin B1 oxime was converted to an amino derivative by using carbodiimide chemistry with 1,3 diamino-2-hydroxypropane. This amino-aflatoxin derivative was then converted to a sulfhydryl compound with 2-iminothiolane and reacted with sulfo-SMCC activated BSA to make the conjugate. The conjugate, at the dilutions specified above, were sprayed in a line onto nitrocellulose at 0.8 µl/cm using a BioDot sprayer.

The control area was sprayed at 25 mm from the bottom of the nitrocellulose at 0.5 to 1.0 mm width. The control area spray solution included protein A conjugated to BSA (BSA-PA) at a ratio of 0.6 to 2 molecules of protein A to BSA. The control area spray solution included 0.42 mg/ml protein.

To prepare the control area reagent 200 mg of protein A was dissolved into 3 ml of 0.16 M borate buffer, pH 8.1, containing 2 mM EDTA. Sulfo-SMCC was dissolved in DMSO and 3.2 mg was added to the protein A solution. This mixture was incubated with stirring for 1.5 hours and then cooled. The protein A-activated S-SMCC reaction was added to 2.4 ml of cold 0.4 M sodium phosphate buffer, pH 5.9, containing 2.1 grams of BSA. The solution pH was adjusted to 6.5-7.0 and reacted overnight at 4° C. with stirring. The reaction was desalted using a high prep desalting column against 10 mM phosphate buffer, pH 6.9, containing 50 mM NaCl and 4% sucrose to a final protein concentration of 50 mg/ml.

For spraying as a control area, the reaction was diluted 40 fold in 10 mM sodium phosphate buffer, pH 7.2, containing 5% sucrose and PROCLIN® 5000. The area was sprayed in a line onto nitrocellulose, using a BioDot sprayer, at 1.0 µl/cm and dried. The control area was sprayed and dried at the same time as the test areas.

Results were read using a ROSA® reader to read reflectance on the strip. The single control area intensity was compared to each of two test area intensities and the results were summed.
Results In Table 1, B (bottom) and M (middle) are the first and second test areas and T (top) is the control area, respectively. The results, intensity values determined using a ROSA® Reader, were as follows:

TABLE 1

| Conc. ppb | B | M | T | T − B | T − M | Result Sum (T − B) + (T − M) |
|---|---|---|---|---|---|---|
| 0 | 3496 | 3164 | 2102 | −1394 | −1062 | −2456 |
| 5 | 3806 | 3812 | 3175 | −631 | −637 | −1268 |
| 10 | 3005 | 3137 | 3266 | 261 | 129 | 390 |
| 20 | 2466 | 2823 | 3269 | 803 | 446 | 1249 |
| 100 | 1742 | 2591 | 4043 | 2301 | 1452 | 3753 |

The curve of the data can be represented by the following formula for calibration of the reader and conversion of reader results into a ppb value.

$$ppb = e^{\left(\frac{Result - c}{a}\right)} - b,$$

where a=1832; b=3; c=−4654.
The constants a, b and c are determined by a curve fit for a model data set and the result is the value from the equation [T minus B plus T minus M] from Table 1.

EXAMPLE 2

The absolute result range can be adjusted, for example so that results above a certain threshold provide results in the positive number range, by adjusting the test areas and control area binding potential. Table 2 below is an example of results where samples above 10 ppb provide a positive intensity value showing that the test is not limited to just determining a quantitative value.

TABLE 2

| Concentration ppb | Result |
|---|---|
| 0 | −2500 |
| 2.5 | −1200 |
| 5 | −1000 |
| 10 | 0 |
| 20 | 1200 |
| 37.5 | 2200 |
| 50 | 2700 |
| 75 | 3400 |
| 100 | 4000 |

In the above table the overall spread between 0 ppb (−2500) to 100 ppb (4000) is 6500.

EXAMPLE 3

In this example various methods for reading and interpreting test results are compared, for example in the case where one test area is used to calculate an overall intensity value and where two tests areas are used to calculate an overall intensity value. results. Table 3 results are, in most cases, the average of three results. The first column shows parts per billion (ppb) concentration of aflatoxin. The second column shows results of a one test area/one control area test with result interpretation by comparison of test area to control area (difference in intensity value between control area and test area). The third column shows results from a two test area/one control area strip with result interpretation by utilizing only the bottom test area result for comparison to the control area and ignoring the middle area result. The fourth and fifth columns show results converted to differences from 0 ppb result. Dilutions for one test area test were 0.035 mg/ml BSA-B1 for test area and 0.25 mg/ml BSA-PA for control area. Dilutions for two test area were 0.035 mg/ml BSA-B1, 0.07 mg/ml BSA-B1 and 0.33 BSA PA for bottom/middle/top areas, respectively. Results show an increase spread in the two test area/one control area test (3266) when only the bottom test area is used as compared to single test area test (2314) as a result of increasing the test zone binding capacity with the addition of the second BSA-B1 test line.

TABLE 3

| Conc. ppb | 1 test area | 2 test area bottom only | 1 test area line diff 0 ppb | 2 test area line diff 0 ppb |
|---|---|---|---|---|
| 0 | −973 | −1104 | 0 | 0 |
| 4.3 | −580 | −689 | 393 | 415 |
| 9.1 | −129 | 43 | 844 | 1147 |
| 12.5 | 129 | 495 | 1102 | 1599 |
| 25 | 723 | 1045 | 1696 | 2149 |
| 25.7 | 502 | 1212 | 1475 | 2316 |
| 50 | 1005 | 1603 | 1978 | 2706 |
| 100 | 1341 | 2162 | 2314 | 3266 |

Table 4 compares results using one test area/one control area test with doubling the difference between the control area and test area intensities (second column), to results using a two test area/one control area strip calculating the sum of the difference between the test area from the control area (third column). Results show an increase spread in the two test area/one control area test. The fourth and fifth columns show the results converted to differences from zero. The test strip dilutions were, as described above, 0.035 mg/ml BSA-B1, 0.07 mg/ml BSA-B1 and 0.33 BSA PA for bottom/middle/top areas, respectively, for the two test area test and 0.03 mg/ml BSA-B1 for test area and 0.25 mg/ml BSA-PA for control area for one test area test. Although the spread is increased by doubling the difference of the control area and test area for the one test area result, error in measurement is also increased.

TABLE 4

| Conc. ppb | 2 × diff 2 test area | 2 test area sum of differences | diff from 0 1 test area | diff from 0 2 test area |
|---|---|---|---|---|
| 0 | −1946 | −2856 | 0 | 0 |
| 4.3 | −1160 | −1558 | 786 | 1299 |
| 9.1 | −258 | −1049 | 1688 | 1807 |
| 12.5 | 258 | −385 | 2204 | 2471 |
| 25 | 1446 | 724 | 3392 | 3580 |
| 25.7 | 1004 | 999 | 2950 | 3855 |
| 50 | 2009 | 1362 | 3955 | 4219 |
| 100 | 2683 | 2256 | 4629 | 5112 |

Table 5 shows individual area intensities at each of the test and control areas in a one test area/one control area test compared to the two test area test/one control area test. The fourth column shows the difference in intensity between the top and bottom areas in the one test area test and the eighth column shows the sum of the difference between the intensity results between the top/middle and top/bottom areas.

TABLE 5

| | 1 test area | | | 2 test area | | | |
|---|---|---|---|---|---|---|---|
| Conc. ppb | Top | Bottom | Result | top | middle | bottom | Result |
| 0 | 3206 | 4179 | −973 | 2111 | 3863 | 3214 | −2856 |
| 4.3 | 3476 | 4056 | −580 | 2590 | 4237 | 3279 | −2337 |
| 9.1 | 3039 | 3168 | −129 | 3065 | 4158 | 3022 | −1049 |
| 12.5 | 3414 | 3285 | 129 | 3186 | 4067 | 2691 | −385 |
| 25 | 3361 | 2638 | 723 | 2942 | 3263 | 1897 | 724 |
| 25.7 | 3170 | 2668 | 502 | 3352 | 3565 | 2139 | 999 |

TABLE 5-continued

| | 1 test area | | | 2 test area | | | |
|---|---|---|---|---|---|---|---|
| Conc. ppb | Top | Bottom | Result | top | middle | bottom | Result |
| 50 | 3505 | 2689 | 815 | 3162 | 3403 | 1560 | 1362 |
| 100 | 3478 | 2137 | 1341 | 3354 | 3260 | 1191 | 2256 |

EXAMPLE 4

The area spacing described in Example 1 (17, 21, and 25 mm—respectively, for bottom/middle/top lines) was compared with the area spacing at 13, 17 and 21 mm bottom/middle/top, respectively. Both sets of areas were sprayed with test area 1 (bottom area)/test area 2 (middle area)/control area (top area) having respective concentrations of 0.0525 mg/ml BSA-B1, 0.084 mg/ml BSA-B1 and 0.42 mg/ml BSA-PA abd tested with 25%, 4000 U beads.

Incubation at 40° C., in a stainless steel incubator block carved to fit the test strips, for 10 minutes for the 13, 17 and 21 mm strip and 12 minutes for the 17, 21 and 25 mm strip. At 10 minutes incubation with the 17, 21 and 25 mm strip, the spread in results (difference between control and test area) from 0-100 ppb as compared to the 12 minute incubation, was lower, therefore, the incubation time was increased to allow more time for the beads to flow across the test strip. When the areas were moved closer to the beads (13, 17 and 21 mm) the flow across the test and control zones is quicker so that a shorter assay time is possible.

TABLE 6

| 17 mm/21 mm/25 mm area spacing | | |
|---|---|---|
| Conc. Ppb | 10 minute incubation | 12 minute incubation |
| 0 | −2501 | −2502 |
| 10 | 261 | 668 |
| 100 | 3083 | 3830 |

TABLE 7

| 13 mm/17 mm/21 mm area spacing | | |
|---|---|---|
| Conc. Ppb | 10 minute incubation | 12 minute incubation |
| 0 | −2462 | −2150 |
| 10 | 961 | 881 |
| 100 | 4941 | 4879 |

EXAMPLE 5

Test results were compared using the area spacing of 13, 17 and 21 mm with 10 minutes incubation to the same area spacing with 8 minutes incubation, both at 40° C. in a stainless steel incubator block carved to fit the test strips. Areas were sprayed with 25%, 4000 U beads and test area 1 (bottom area)/test area 2 (middle area)/control area (top area) respective concentrations are, respectively of 0.057 mg/mL BSA-B1, 0.091 mg/mL BSA-B1, and 0.417 mg/mL BSA-PA, respectively.

Results in the following tables show that 8 minute results or 10 minute results are possible and that incubation at room temperature for an additional 2 minutes had little impact on sensitivity. Although the examples used incubation at 40° C., other temperatures can also be used.

TABLE 8

13 mm/17 mm/21 mm area spacing with a 10 minute incubation

| Conc. ppb | Top area | Middle area | Bottom area | Result |
|---|---|---|---|---|
| 0 | 1999 | 4214 | 3933 | −4150 |
| 5 | 2651 | 3996 | 3396 | −2091 |
| 10 | 3089 | 3889 | 3062 | −774 |
| 20 | 3494 | 3558 | 2528 | 901 |
| 50 | 3866 | 2991 | 1671 | 3069 |
| 100 | 3749 | 2479 | 992 | 4027 |
| 200 | 4263 | 2368 | 739 | 5420 |

TABLE 9

13 mm/17 mm/21 mm area spacing with an 8 minute incubation

| Conc. ppb | Top area | Middle area | Bottom area | Result |
|---|---|---|---|---|
| 0 | 1740 | 4019 | 3913 | −4452 |
| 5 | 2521 | 3959 | 3491 | −2409 |
| 10 | 3094 | 3771 | 3196 | −779 |
| 20 | 3141 | 3440 | 2417 | 425 |
| 50 | 3524 | 2731 | 1425 | 2892 |
| 100 | 3975 | 2743 | 1275 | 3933 |
| 200 | 4170 | 2131 | 751 | 5459 |

TABLE 10

13 mm/17 mm/21 mm area spacing with an 8 minute incubation plus 2 minutes

| Conc. ppb | Top area | Middle area | Bottom area | Result |
|---|---|---|---|---|
| 0 | 1941 | 4211 | 4095 | −4423 |
| 5 | 2892 | 4170 | 3630 | −2016 |
| 10 | 3591 | 4030 | 3441 | −289 |
| 20 | 3421 | 3518 | 2465 | 860 |
| 50 | 3752 | 2769 | 1420 | 3315 |
| 100 | 4209 | 2823 | 1298 | 4297 |
| 200 | 4442 | 2153 | 764 | 5967 |

DESCRIPTION OF THE DRAWINGS

FIG. 1 shows a test strip apparatus 8, comprised of nitrocellulose membrane 3, POREX® 7, sample application pad 1, and disposal pad 6 attached to solid support 2. Sample is contacted to sample pad-sponge 1. Sample flows from sample application pad 1 to POREX®-7 containing mobile phase receptor. A portion of receptor will bind analyte from the sample and flow along the nitrocellulose membrane 3 to test areas 9 and 4. A portion of receptor unbound by sample analyte will bind to the test areas. Remaining unbound receptor and analyte-receptor complex will flow to control area 5. A portion of said unbound receptor and a portion of analyte-receptor complex, will bind at the control area. Remaining unbound receptor or analyte-receptor complex will flow the absorbent pad 6. The control area is compared to the test areas to determine a result. Although not clear from FIG. 1, the two test areas and one control area can be evenly spaced from one another or spaced in other variations.

Figure 2A:
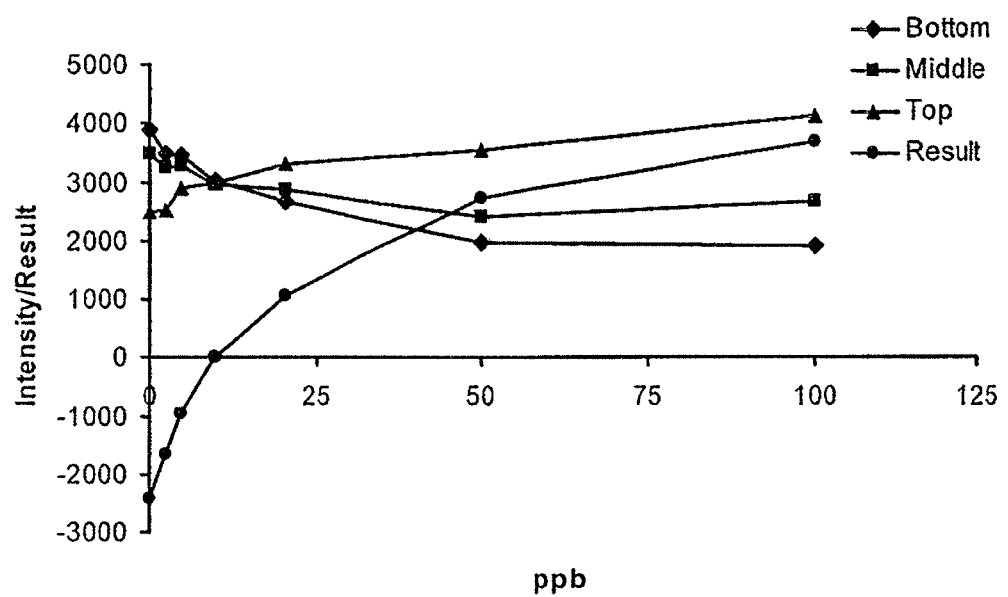
FIG. 2A are graphs relating intensity of color development on a test strip (Y axis), with 2 test areas (bottom and middle) and a control area (top), to aflatoxin concentration in samples (X axis).

FIG. 2A is a graph relating intensity of color development on a test strip to aflatoxin concentration in samples. The bottom test area of the test strip, indicated with a diamond shape on the graph, is the first test area contacted by the mobile phase in the flow on the strip. The middle area, indicated with a square shape, is the second test area contacted by the mobile phase in the flow on the strip. The top area, indicated with a triangle shape, is the control area and is the last area contacted by the sample in the flow on the strip. The result line, indicated by a circular shape, shows the results which are calculated by measuring the difference in signal intensity between each test area and the control area and summing the differences. The bottom area, at 0 ppb, has the highest intensity and the middle area has the second highest intensity. As the concentration of analyte, in this example aflatoxin, increases there is a steady loss in intensity at both the bottom area and middle area (the test areas), reflecting the inhibition of labeled receptor from binding to the test areas. Results to 50 ppb show relatively constant inhibition at the test areas. That is, in this data set, there is little difference in test area intensities between 50 ppb and 100 ppb while the control area intensity changes significantly from 50 ppb to 100 ppb, providing the test result difference from 50 ppb to 100 ppb. As is shown by the results line (calculated by deducting the bottom area intensity from the top area intensity and deducting the top area intensity from the middle area intensity, and then adding the two differences), the intensity difference between each of the test areas and the control area provides the sensitivity to distinguish, in this particular test strip, between aflatoxin concentrations between 0 ppb and 100 ppb.

Figure 2B:
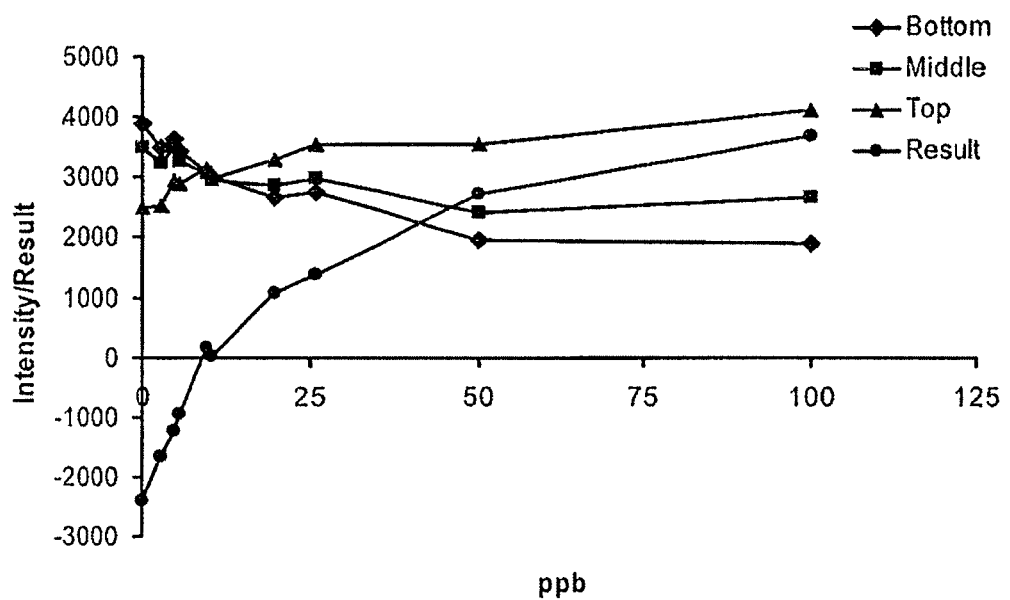
FIG. 2B are graphs of the results from the same experiments as in FIG. 2A with additional concentrations included.

FIG. 2B is a graph of the results from the same experiments as in FIG. 2A with additional concentrations included. Additional data points show that the results are corrected for variations in area intensity that may have resulted from flow differences within the test strip or from sample variation resulting from different sources of raw materials tested. For example, the results (circle) at around Intensity/Result −1000 are corrected from the aberrant results in the control and test areas.

Figure 3A:
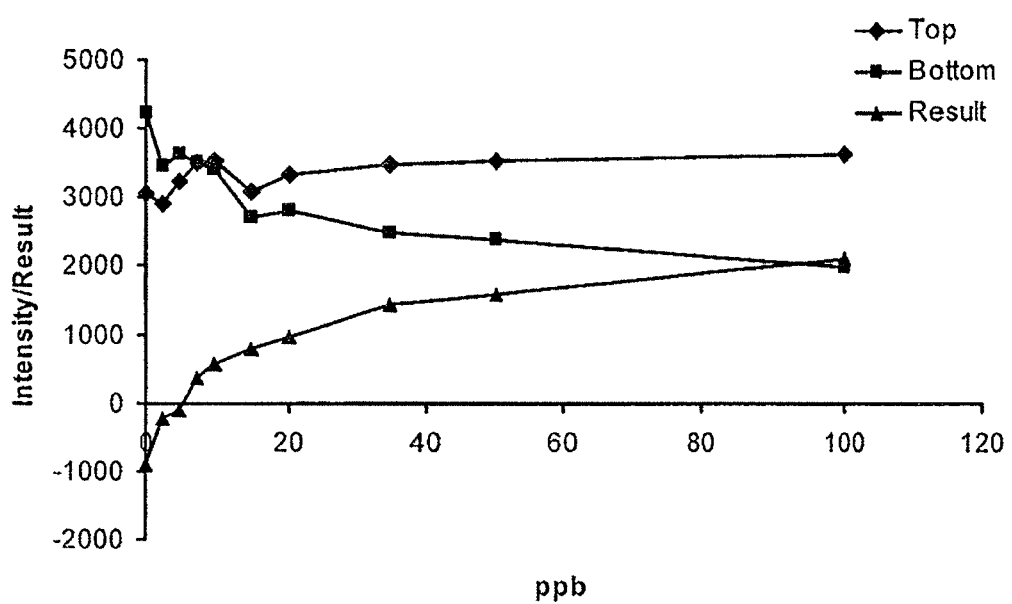
FIG. 3A are graphs relating intensity of color development on a test strip (Y axis), with 1 test area (bottom) and a control area (top), to aflatoxin concentration in samples (X axis).

FIG. 3A is a graph of the results from experiments with a single test area and control area using a 0.035 mg/ml conjugate-BSA-B1 on the test area and 0.025 mg/ml BSA-PA) on the control area. The result area (top-bottom), indicated by the triangle, reflects lower sensitivity than the result line in FIGS. 2A and 2B. That is, there is significantly less spread (difference between control area and test area), in the one test area test, at varying concentrations as compared to the two test area test.

Figure 3B:
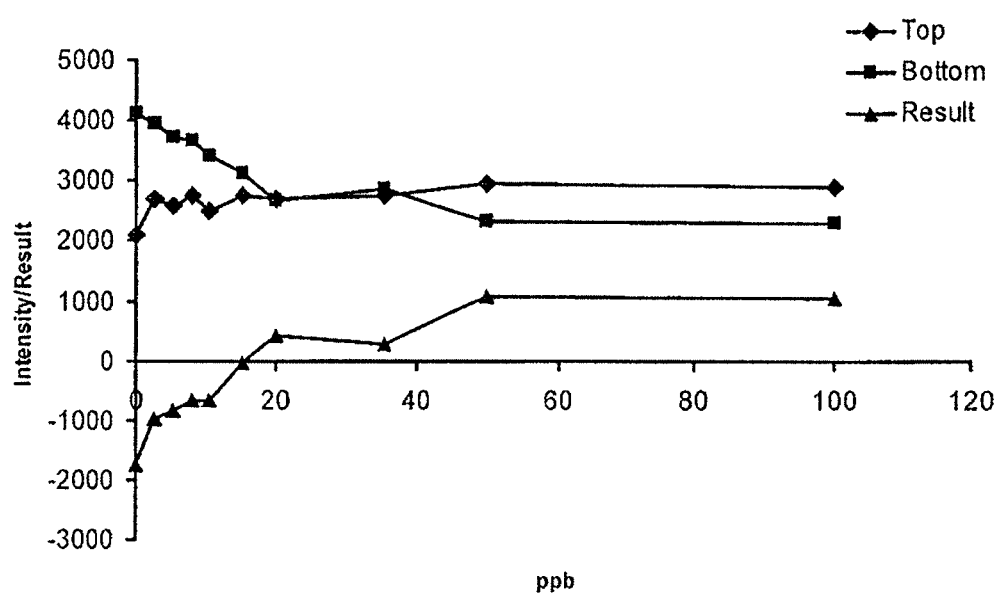
FIG. 3B are graphs similar to 3A and showing that reducing the concentration of capture agent in the top area reduces the intensity of color development at the top line but does not significantly change the spread between results at various concentrations.

FIG. 3B demonstrates how changing the concentration of the top area, from 0.025 mg/ml to 0.016 mg/ml BSA-PA, indicated by the diamond, impacts test results, indicated by the triangle. The top area intensity at 0 ppb starts at 2000, rather than 3000 (as in FIG. 3A). As with FIG. 3A, the result line, indicated by the triangle, is less sensitive than the result line in FIG. 2A and FIG. 2B. There is, therefore, significantly less spread (difference) between results at varying concentrations as compared to using two test areas. The comparison between FIG. 3A and FIG. 3B shows that changing the concentration at the control area shifts the lines—the top area intensity at 0 ppb (y intercept) starts at 2000, rather than 3000. Changing the concentration at the control area, however, does not significantly change the spread between results at various concentrations. For example, in FIG. 3A, the result at 0 ppb is −1000 and the result at 100 ppb is 2000, providing a 3000 point spread. In FIG. 3B the result at 0 ppb is −2000, and the result at 100 ppb is 1000, again providing a 3000 point spread. This is compared to, in FIG. 2A and FIG. 2B, an approximately 6000 point spread between 0 ppb and 100 ppb. Thus, the second test area can provide a significant increase in spread and, therefore, can provide more accuracy from concentration to concentration. That is, a larger spread allows a greater margin of error without affecting test results. The larger margin of error is particularly important, for example, when samples and results are variable and when quantitation is required.

Figure 4:
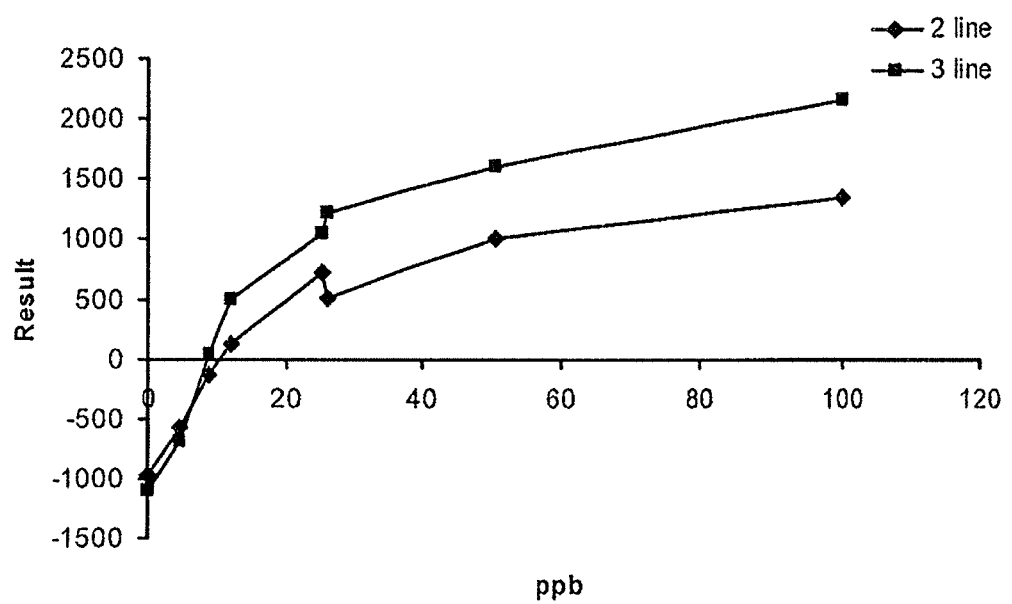
FIG. 4 is a graph comparing results from a single test area/control area test for aflatoxin (2 line ave) with a two test area/single control area test for aflatoxin (3 line ave), where only the first test area, of the two test area test, was used to calculate results. This graph demonstrates that even when the second test area is not used to calculate results, the added binding capacity created by the presence of the second test area can help increase the detection range of the test.

FIG. 4 is a graph comparing results from a single test area/control area test for aflatoxin with a two test area/single control area test for aflatoxin, where only the first test area was used to calculate results. This graph demonstrates that even when the second test area is not used to calculate results, the added binding capacity created by the presence of the second test area can help increase the detection range of the test. The inconsistency in the data—the one test area test shows a drop in intensity from 25 ppb to 25.7 ppb—demonstrates the importance of a larger spread when testing multiple sample lots.

The invention claimed is:

1. A method for the analysis of a liquid sample for the presence of an analyte comprising the steps of:
   a) contacting the sample with a receptor to form a mobile phase, the receptor characterized by an ability to bind to the analyte to provide, in the mobile phase, a receptor-analyte complex;
   b) contacting the mobile phase with a solid support, the solid support configured to allow lateral flow of the mobile phase to a first test area, a second test area and a control zone, the first test area, the second test area and the control zone configured on the solid support in a spaced apart relationship and each comprising a capture agent immobilized on the solid support, the first and the second test area capture agents characterized in that the capture agent has greater binding affinity to the receptor than to the receptor-analyte complex, the control zone capture agent characterized in that the affinity to the receptor is equivalent to the affinity to the receptor-analyte complex, the solid support configured to allow the mobile phase to flow from the first test area to the second test area on the solid support and from the second test area to the control zone on the solid support;
   c) prior to, currently with, or subsequent to steps (a) and (b), tagging the receptor with a label, the label characterized in that it provides a detectable signal when the receptor is bound to any of the first test area capture agent, the second test area capture agent and the control zone capture agent; and
   d) measuring the intensity of the detectable signal at each of the first test area, the second test area and the control zone,
   wherein the intensity of the detectable signals in the test areas are inversely related to a concentration of the analyte in the sample.

2. The method of claim 1 wherein the signal intensities are measured by an electronic test instrument and wherein the instrument: (i) measures intensity at each of the two test areas and the control zone; (ii) sums the intensity at the two test areas; and (iii) compares the sum of the signal intensities at the first test area and the second test area with the signal intensity at the control zone to determine a test result.

3. The method of claim 2 further comprising using the test result to determine the concentration of the analyte in the sample.

4. The method of claim 3 wherein the concentration of the analyte in the sample is determined by a comparison with a predefined test parameter.

5. The method of claim 1 wherein the signal comprises a visible signal and wherein the label comprises a gold particle.

6. The method of claim 1 wherein a test result is determined by comparing the signal intensities at the first test area and the second test area with the signal intensity at the control zone.

7. The method of claim 1 wherein a test result is determined by comparing the signal intensities at one of either the first test area or the second test area with the signal intensity at the control zone.

8. The method of claim 1 wherein a test result, related to the signal intensity, is provided by an electronic instrument, and wherein the instrument: (i) measures the signal intensities; (ii) calculates the difference between the first test area intensity and the control zone intensity; (iii) calculates the difference between the second test area intensity and the control zone intensity; (iv) sums the results of (ii) and (iii) to arrive at the test result; (v) determines the concentration of analyte in the sample by comparing the test result to a predetermined value; and (vi) displays the analyte concentration.

9. The method of claim 8 wherein the test result is a digital result.

10. The method of claim 8 wherein the instrument comprises a reflectance reader.

11. The method of claim 1 wherein the receptor is labeled prior to contact with the liquid sample.

12. The method of claim 1 wherein the first test area capture agent is the same as the second test area capture agent.

13. The method of claim 12 wherein the first test area capture agent and the second test area capture agent are in the same concentration.

14. The method of claim 12 wherein the first test area capture agent and the second test area capture agent are in different concentrations.

15. The method of claim 1 wherein the first test area capture agent and the second test area capture agent are representative analyte or analog thereof.

16. The method of claim 1 wherein the first test area capture agent and the second test area capture agent are different capture agents.

17. The method of claim 1 wherein the analyte comprises a mycotoxin.

18. The method of claim 1 wherein the liquid sample comprises a liquid extract.

19. The method of claim 8 wherein the concentration is determined using a formula, the formula comprising:

$$\text{concentration} = e^{\left(\frac{Result-c}{a}\right)} - b$$

where a, b, and c are constants.

20. The method of claim 3 wherein the test result is a quantitative test result is determined within a range of acceptable error.

21. The method of claim 8 wherein the test result is a quantitative test result is determined within a range of acceptable error.

22. The method of claim 21 wherein the concentration is determined using a formula, the formula comprising:

$$\text{concentration} = e^{\left(\frac{Result-c}{a}\right)} - b$$

Where a, b, and c are constants.

* * * * *